United States Patent [19]

Park

[11] Patent Number: 5,419,819
[45] Date of Patent: May 30, 1995

[54] SELF-REGENERATING COLUMN CHROMATOGRAPHY

[75] Inventor: Woo K. Park, Centerville, Ohio

[73] Assignee: The United States of America as represented by the United States Department of Energy, Washington, D.C.

[21] Appl. No.: 214,261

[22] Filed: Mar. 17, 1994

[51] Int. Cl.$^6$ .............................................. B01D 5/00
[52] U.S. Cl. ........................... 204/157.2; 204/157.46; 204/157.49; 376/189
[58] Field of Search ............ 204/157.2, 157.46, 157.49; 376/188, 189; 423/6, 8; 210/682, 253

[56] References Cited

U.S. PATENT DOCUMENTS

| | | | |
|---|---|---|---|
| 3,953,568 | 4/1976 | Seko et al. | 423/7 |
| 3,971,842 | 7/1976 | Ewbank | 423/7 |
| 4,087,357 | 5/1978 | Barrett et al. | 210/32 |
| 4,280,984 | 7/1981 | Miyake et al. | 423/6 |
| 4,302,424 | 11/1981 | Miyake et al. | 422/159 |
| 4,464,343 | 8/1984 | Hitchcock et al. | 423/3 |
| 4,537,911 | 8/1985 | Chonde | 521/28 |
| 5,021,163 | 6/1991 | Anderson et al. | 210/661 |
| 5,108,616 | 4/1992 | Kunz | 210/678 |

OTHER PUBLICATIONS

W. M. Rutherford, "Separation of the Stable Isotopes of Chlorine, Sulfur, and Calcium", Stable Isotopes, 1982, pp. 703-709.
B. E. Jepson et al., "Calcium Hydroxide Isotope Effect in Calcium Isotope Enrichment by Ion Exchange", *Separation Science and Technology*, vol. 19, Nos. 2&3, 1984, pp. 173-181.
T. Oi et al., "Magnesium Isotope Fractionation in Cation-Exchange Chromatography", *Separation Science and Technology*, vol. 22, No. 11, 1987 pp. 2203-2215.
D. M. Brown et al., "Anion-Cation Separations on a Mixed Bed Alumina-Silica Column", *Journal of Chromatography*, vol. 466, 1989, pp. 291-300.
T. Oi et al., "Fractionation of Strontium Isotopes in Cation-Exchange Chromatography", *Separation Science and Technology*, vol. 27, No. 5, 1992, pp. 631-643.
W. K. Park et al., "Separation of Nitrogen Isotopes by Displacement Band Chromatography", *Separation Science and Technology*, vol. 23, Nos. 12 & 13, 1988, pp. 1875-1889.
W. K. Park et al., "The Effects of Operating Parameters on Nitrogen Isotopes Separation by Displacement Band Chromatography", *Separation Science and Technology*, vol. 25, Nos. 13-15, 1990, pp. 1909-1918.
W. K. Park et al., "Separation of Sulfur Isotopes by Displacement Band Chromatography", *Proceedings of the International Symposium on Isotope Separation and Chemical Exchange Uranium Enrichment*, Special Issue 1, Oct. 29, 1990, pp. 1-6.
W. K. Park et al., "Displacement Band Chromatography of Hydrogen Sulfites For Enrichment of Sulfur Isotopes", *Separation Science and Technology*, vol. 28, Nos. 1-3, 1993, pp. 477-486.
F. H. Spedding et al., "A Laboratory Method for Separating Nitrogen Isotopes by Ion Exchange", *J. Am. Chem. Soc.*, vol. 77, Dec. 5, 1955, pp. 6125-6132.

*Primary Examiner*—Donald P. Walsh
*Assistant Examiner*—Meena Chelliah
*Attorney, Agent, or Firm*—Armand McMillan; James H. Chafin; William R. Moser

[57] ABSTRACT

The present invention provides a process for treating both cations and anions by using a self-regenerating, multi-ionic exchange resin column system which requires no separate regeneration steps. The process involves alternating ion-exchange chromatography for cations and anions in a multi-ionic exchange column packed with a mixture of cation and anion exchange resins. The multi-ionic mixed-charge resin column works as a multi-function column, capable of independently processing either cationic or anionic exchange, or simultaneously processing both cationic and anionic exchanges. The major advantage offered by the alternating multi-function ion exchange process is the self-regeneration of the resins.

18 Claims, No Drawings

SELF-REGENERATING COLUMN CHROMATOGRAPHY

BACKGROUND OF THE INVENTION

This invention was completed in conjunction with the United States Department of Energy. The contract number is DE-AC04-76DP00053.

FIELD OF THE INVENTION

Ion-exchange chromatography is a well-established separation technique, based on ion-exchange between a stationary resin phase and a mobile liquid phase. This technique has widely been used for separating chemical components that are soluble and ionic from their mixture. The separation of chemical components in ion-exchange chromatography is generally accomplished by passing their mixture through a column packed with an ion-exchange resin. Since chemical components have different affinities to the resin, a mixture of chemical components can be separated as it moves along the ion-exchange resin column. Moreover, the availability of high-performance ion-exchange resins has made this technique quite attractive for separating and enriching components, such as isotopes, which have very small separation factors.

There are, however, several shortcomings involved in this technique. One of them is the need for the regeneration of the resin column after each use. The spent resin in the column needs to be converted back to the initial form if the column is to be reused, as in a cyclic mode of operation. The regeneration step typically requires washing of the resin with a strong acid or base. The ions adsorbed on the resin during the separation step should be replaced by cations such as $H^+$ of an acid or anions such as $OH^-$ of a base, depending on the type of resin to be regenerated (cationic or anionic). Therefore, a large amount of excess acid or base solution is usually passed through the resin column, generating a large volume of chemical waste in the regeneration step. Thus, the processes based on this technique would, in general, suffer from high costs for chemicals, deionized water, and waste handling in addition to the need for extra time and effort for regeneration. This may be the main drawback that limits the wide use of the ion-exchange chromatographic technique on a commercial scale.

Examples of Current Technologies for Separations

1) Nitrogen Isotope Separation

Nitrogen isotopes can be separated and enriched by using the ion exchange chromatographic technique described by W. K. Park and E. D. Michaels in 23 *Sep. Sci. and Technl.* 1875 (1988) and by W. K. Park, E. D. Michaels, and C. P. Carroll in 25 *Sep. Sci. and Technl.* 1909 (1990). This is achieved through the formation of an ammonium hydroxide band in an ion-exchange column and the distribution of nitrogen isotopes within this band. A predetermined amount of ammonium hydroxide ($NH_4OH$) solution is fed into a column of a cation exchange resin conditioned in the hydrogen form, and is displaced by a sodium hydroxide (NaOH) solution, forming a moving band.

The work scheme is analogous to a conventional distillation system, where the boundaries of the moving $NH_4OH$ feed band perform like the reflux units. Thus, as in a reboiler unit, ammonium ions ($NH_4^+$) of the $NH_4OH$ solution are retained in the resin phase as if forming an upward flux relative to the downward moving band, at the front boundary of the band. Similarly, as in a condenser unit, the $NH_4^+$ ions are released from the resin by the $Na^+$ ions of an NaOH displacer solution at the rear boundary of the band, and converted to $NH_4OH$ for downward flow in the liquid phase. The counter-current flow of ions and solution is thus developed as the band moves down the resin column, forming a longitudinal isotopic profile. The $^{15}N$ isotope is enriched in the rear of the band and the $^{14}N$ isotope in the front.

Various major reactions occur at different parts of the band.

At the front boundary of the band:

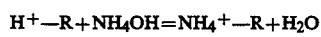
$$H^+ - R + NH_4OH = NH_4^+ - R + H_2O$$

where $-R$ denotes the cation resin phase

Within the band:

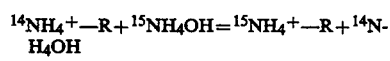
$$^{14}NH_4^+ - R + {}^{15}NH_4OH = {}^{15}NH_4^+ - R + {}^{14}NH_4OH$$

At the rear boundary of the band:

$$NH_4^+ - R + Na^+ + OH^- = Na^+ - R + NH_4OH$$

After each run as well as before the start of the first run, the resin in the column is regenerated (or converted) to the initial H-form by washing with a sulfuric acid ($H_2SO_4$) or hydrochloric acid (HCl) solution. The $H^+$ ions of the $H_2SO_4$ or HCl replace the $Na^+$ ions on the resin adsorbed from the NaOH displacer solution as the acid solution flows down the resin column. Once the low pH value of the column effluent indicates that the regeneration is completed, the excess $H_2SO_4$ or HCl remaining in the resin column is removed with a deionized water flush, making the resin column ready for the next run.

2) Sulfur Isotope Separation

Sulfur isotopes can be separated and enriched by using the same ion-exchange chromatographic technique as is used for nitrogen isotope separation. This information was presented at the International Symposium on Isotope Separation and Chemical Exchange Uranium Enrichment, Oct. 29–Nov. 1, 1990, Tokyo Institute of Technology, Tokyo, Japan by W. K. Park and E. D. Michaels and published by W. K. Park and E. D. Michaels in 28 (1-3) *Sep. Sci. and Technl.* 477 (1993). In this separation, however, a sulfurous acid (conventionally noted as $H_2SO_3$) solution is fed into a column of an anion exchange resin conditioned in the hydroxide form and displaced by an $H_2SO_4$ or HCl solution, forming a moving band. It also develops a counter-current flow within the band boundaries, with in-situ refluxing. Bisulfite ($HSO_3^-$) ions are released from the resin by an $H_2SO_4$ or HCl solution, and returned to the liquid phase for downward flow at the rear boundary. At the front boundary, the $HSO_3^-$ ions of the $H_2SO_3$ solution are retained in the resin phase, forming an upward flux relative to the downward moving band. Therefore, as the band moves down the resin column, the counter-current flow of solution and ions is continued, inducing sulfur isotopic exchange between these two currents in two phases. A longitudinal isotopic profile is developed along the length of the band in which the $^{34}S$ isotope is enriched in the rear and the $^{32}S$ isotope in the front. The controlling reactions are:

At the rear boundary of the band:

$$HSO_3^- \text{—} R' + H_2SO_4 = HSO_4^- \text{—} R' + H_2SO_3$$

where —R' denotes anion resin phase and $H_2SO_3$ denotes aqueous $SO_2$.

Within the band:

$$H^{32}SO_3^- \text{—} R' + H_2{}^{34}SO_3 = H^{34}SO_3^- \text{—} R' + H_2{}^{32}SO_3$$

At the front boundary of the band:

$$OH^- \text{—} R' + H_2SO_3 = HSO_3^- \text{—} R' + H_2O$$

The regeneration of spent anionic resin is achieved by washing with an NaOH solution. $OH^-$ ions of the NaOH solution replace $HSO_4^-$ or $Cl^-$ ions retained on the resin from an $H_2SO_4$ or HCl displacer solution. Any excess acid remaining in the resin column after regeneration is flushed out by deionized water.

SUMMARY OF THE INVENTION

This disclosure describes a process for treating both cations and anions by using a self-regenerating resin column or column system which requires no separate regeneration steps. The process involves ion-exchange chromatography for cations and anions in a multi-ionic exchange column packed with exchange resin(s) having mixed charges. The mixed-charge resin column works as a multi-function column, capable of independently processing either cationic or anionic exchange, or simultaneously processing both cationic and anionic exchanges. The major advantage offered by the multi-function process is the self-regeneration of the mixed-charge resins which occurs automatically during alternating ion exchanges. The separate regeneration steps normally required for resins in typical ion exchange chromatographic processes are no longer needed in this process.

For example, while nitrogen isotopes present in ammonium cations are separated in the cation resin phase of the mixed-charge resin column, the anion resin phase is concurrently regenerated by the nitrogen feed and displacer solutions being processed for the cationic exchange enrichment of nitrogen isotopes. Similarly, while sulfur isotopes present in bisulfite anions are separated in the anion resin phase, the cation resin phase is regenerated by the sulfur feed and displacer solutions.

In this process scheme of self-regenerating, multi-function, column chromatography, cation and anion feed bands can alternately be displaced in the column for the desired isotopic enrichments, permitting each ionic resin phase to be regenerated during the separation steps. The alternating ion exchange with self-regeneration should also allow a continuous cyclic operation of the process for the low-cost isotopic enrichment and ionic solution processing.

The process can be incorporated into single- or multi-column systems for the continuous production of enriched isotopes or processing ionic solutions. It may be possible to recycle some of the displacer solutions back to the column under certain conditions, for an additional reduction of the production costs.

The cost of enriching isotopes as well as processing anions and cations can significantly be reduced by utilizing this self regenerating process, since it requires: 1) no regenerant chemicals; 2) lesser efforts in chemical waste handling; 3) lesser amounts of deionized water; and 4) fewer resin columns per train. The drawback of this method is, of course, some decrease of the separation efficiency that results from a slightly higher axial dispersion in the mixed-charge bed column.

The present invention provides a process for treating ions comprising the steps of: (1) delivering at least one ionic feed solution, in either acidic or alkaline state, to a mixed-charge bed of oppositely-charged resins; (2) delivering at least one ionic displacer solution, in the same acidic or alkaline state as the ionic feed solution to the mixed-charge bed, and sequentially to the ionic feed solution; and (3) recovering desired ion or ions. Preferred is a process as described in this paragraph, wherein the ionic feed solution comprises specific isotopes in cationic, anionic or mixed (salt) form and the isotopes are separated and enriched within the ionic feed band during the processing, for recovery. Most preferred is a process wherein the specific isotopes in mixed (salt) form are separated, enriched and recovered from each ionic feed solution simultaneously.

The present invention also provides a process for treating ions comprising the steps of: (1) delivering at least one first ionic feed solution in either acidic or alkaline state, to a mixed-charge bed; (2) delivering a first ionic displacer solution in the same acidic or alkaline state as the first ionic feed solution, to the mixed-charge bed, and sequentially to the first ionic feed solution; and (3) delivering at least one second ionic feed solution having the acidic or alkaline state opposite to the first ionic feed and displacer solutions to the mixed-charge bed, and sequentially to the first ionic displacer solution; and (4) delivering a second ionic displacer solution having the same acidic or alkaline state as the second ionic feed solution, to the mixed-charge bed, and sequentially to the second ionic feed solution; and (5) repeating steps (1) through (4) as many times as desired, as long as the pairs of steps are alternating and the terminal step is either (2) or (4); and (6) recovering desired ions.

Preferred embodiments of the process described in the preceding paragraph include one in which ionic feed solutions comprise specific isotopes in cationic, anionic or mixed (salt) form and the isotopes are separated and enriched within the ionic feed band during the processing, for recovery. Also preferred is a process wherein the ionic feed solutions comprise multiple solutions in the same acidic or alkaline state which move together, but in separate bands. However, another embodiment which is preferred is a process wherein steps (1) through (4) occur one time only or wherein the mixed-charge bed comprises two resins with opposite charges. A process wherein the mixed-charge bed comprises one resin with two charges is also preferred. When multiple solutions are utilized, it is also preferable that the multiple solutions comprise specific isotopes in cationic, anionic or mixed (salt) form in each solution and the isotopes are separated and enriched within each solution band during the processing, for recovery.

A more preferred process includes isotopes which are separated, enriched and recovered from each ionic feed solution in an alternating cycle of alkaline displacer solutions and acidic displacer solutions, not necessarily in that order, but ensuring that an ionic feed solution in alkaline or neutral state is displaced by an alkaline displacer solution and an ionic feed solution in acidic or neutral state by an acidic displacer solution. Specifically preferred is an alternating process wherein the first and second ionic feed solutions comprise nitrogen isotopes in alkaline state and sulfur isotopes in acidic state, respectively. Also preferred is a process wherein the ionic feed solutions comprise isotopes chosen from the group consisting of: calcium, strontium, magnesium, chlorine, and bromine.

A more preferred two-resin process is one in which the two resins have equal or unequal capacities. A specifically preferred embodiment of the present invention is one which utilizes the sulfonated polystyrene-divinyl benzene copolymer resin and the aminated polystyrene-divinyl benzene copolymer resin. Particularly, a 12% crosslinked version of both copolymer resins are preferred.

The following are definitions of terms used in this disclosure:

"Ionic feed solution"—a solution of ions having an acidic, alkaline or neutral state. Moreover, ionic feed solution includes a single solution or multiple solutions of cations and anions. For example, each ionic feed solution may contain separable isotopes in cationic, anionic or mixed form.

"Displacer solution"—a solution of ions in acidic, alkaline or neutral state, which have a binding affinity greater than or equal to the binding affinity of the feed ions intended to be displaced. "Displacer solution" includes a single solution of cations and anions.

"Mixed-charge resin column" or "mixed-charge bed"—any apparatus wherein at least one resin containing two charges is operatively designed so that at least one type ion will bind to the resin or resins.

DETAILED DESCRIPTION OF THE INVENTION

The present invention provides a process for treating ions comprising the steps of: (1) delivering at least one ionic feed solution, in either acidic or alkaline state, to a mixed-charge bed of oppositely-charged resins; (2) delivering at least one ionic displacer solution, in the same acidic or alkaline state as the ionic feed solution to the mixed-charge bed, and sequentially to the ionic feed solution; and (3) recovering desired ion or ions. A process as described in this paragraph, wherein the ionic feed solution comprises specific isotopes in cationic, anionic or mixed (salt) form and the isotopes are separated and enriched within the ionic feed band during the processing, for recovery, is preferred. Most preferred is a process wherein the isotopes of two different elements are separated, enriched and recovered from a single mixed ionic feed solution simultaneously.

As those skilled in the art will realize, most of the apparatus and materials utilized in the claimed process are familiar. Skilled artisans are familiar with column chromatography, including various configurations of apparatus. For example, displacement chromatography, elution chromatography, and breakthrough chromatography are commonly known. Moreover, delivery of solutions to columns and recovery of ions from columns are also known by those in the art.

The present process is not limited to any configuration of apparatus, except that the apparatus must include a mixed-charge bed. The mixed-charge bed may be implemented in the same manner as a single-charge bed. The article published by F. H. Spedding et al., in 77 J. Am. Chem. Soc. 6125 (1955) gives an example of single-charge bed implementation.

Furthermore, the process is not dependent on any special preparation of solutions. Preparation of solutions is known in the art; any means for preparing solutions utilized in the present process is acceptable.

The present invention also provides a process for treating ions comprising the steps of: (1) delivering at least one first ionic feed solution in either acidic or alkaline state, to a mixed-charge bed; (2) delivering a first ionic displacer solution in the same acidic or alkaline state as the first ionic feed solution, to the mixed-charge bed, and sequentially to the first ionic feed solution; and (3) delivering at least one second ionic feed solution having the acidic or alkaline state opposite to the first ionic feed and displacer solutions to the mixed-charge bed, and sequentially to the first ionic displacer solution; and (4) delivering a second ionic displacer solution having the same acidic or alkaline state as the second ionic feed solution, to the mixed-charge bed, and sequentially to the second ionic feed solution; and (5) repeating steps (1) through (4) as many times as desired, so long as the pairs of steps are alternating and the terminal step is either (2) or (4); and (6) recovering desired ions. Delivery of multiple solutions is known in the art. In the past, however, regeneration of the initial charge of the resin would have to take place in a separate step. The present invention eliminates the extra step of regeneration, and allows for a continuous process.

Preferred embodiments of the process described in the previous paragraph include one in which ionic feed solutions comprise specific isotopes in cationic, anionic or mixed (salt) form and the isotopes are separated and enriched within the ionic feed band during the processing, for recovery. Also preferred is a process wherein the first ionic feed solution comprises multiple solutions in the same acidic or alkaline state which move together, but in separate bands. However, another embodiment which is preferred is a process wherein steps (1) through (4) occur one time only or wherein the mixed-charge bed comprises two resins with opposite charges. A process wherein the mixed-charge bed comprises one resin with two charges is also preferred. When multiple solutions are utilized, it is also preferable that the multiple solutions comprise specific isotopes in cationic, anionic or mixed (salt) form in each solution and the isotopes are separated and enriched within each solution band during the processing, for recovery.

A more preferred process includes isotopes which are separated, enriched and recovered from each ionic feed solution in an alternating cycle of alkaline displacer solutions and acidic displacer solutions, not necessarily in that order, but ensuring that an ionic feed solution in alkaline or neutral state is displaced by an alkaline displacer solution and an ionic feed solution in acidic or neutral state by an acidic displacer solution. Specifically preferred is an alternating process wherein the first and second ionic feed solutions comprise nitrogen in alkaline state and sulfur in acidic state, respectively. Also preferred is a process wherein the ionic feed solutions comprise isotopes chosen from the group consisting of: calcium, strontium, magnesium, chlorine, and bromine.

Skilled artisans will realize that all materials necessary to implement the present process may be purchased from commercial sources. Companies such as Aldrich and Fisher Scientific are widely known as suppliers of materials. Moreover, many of the chemicals, such as those useful as displacer solutions, may be synthesized by methods known in the art. Columns may be obtained from Valco Instrument Company or Omnifit, for example.

A more preferred two-resin process is one in which the two resins have equal or unequal capacities. A specifically preferred embodiment of the present invention is one which utilizes the sulfonated polystyrene-divinyl benzene copolymer resin and the aminated polystyrene-divinyl benzene copolymer resin. Particularly, a 12% crosslinked version of both copolymer resins is preferred. The resins in this category offer several advantages: high chemical and mechanical stability, high exchange capacity, fast exchange rate and wide availability.

A number of resin characteristics are considered to affect the performance of the resin column for separation. These include the physical and chemical features of the resin such as resin particle size, pore structure, crosslinkage, ionic group and capacity. However, any mixed-charge resin combination is contemplated as within the scope of the present invention.

To elaborate on the contemplated characteristics, resin size is considered an important factor because the smaller size resin offers larger specific surface area, shorter diffusion distance, and smaller void volume when packed in a column; this helps separation efficiency. Moreover, the degree of crosslinking, represented by the percentage of crosslinking agent in the copolymer matrix, affects both the mobility of ions in the resin (and hence separation) and the physical stability of the resin. The competing effects (hence selecting the crosslinkage) require tradeoff to ensure the desired separation efficiency while maintaining physical stability.

Furthermore, the use of smaller-sized resins greatly enhances the extent of separation, increases separative power and decreases the height equivalent to theoretical plate (HETP). By selecting an optimum degree of crosslinking for these resins, an enhanced separation can be achieved within reasonable process conditions. As skilled artisans are aware, singly charged resins varying in size and crosslinkage can be obtained from various sources, including Bio-Rad Laboratories and Benson Company.

The HETP can further be decreased by lowering the superficial velocity and/or displacer concentration. However, this may reduce the separative power also. The band velocity, which is a function of superficial velocity and concentration, may be used as a process variable in controlling HETP. The ratio of band velocity/HETP, may be adjusted in optimizing the process conditions for a desired separation. Based on the large separative power associated with the small resins, the size of resin column required to perform a given separation may be greatly reduced using small resins with an optimum crosslinkage. The column size requirement may also be reduced to a certain extent by increasing the displacer concentration. However, the superficial velocity appears to have insignificant impact on the column sizing while having much influence on the process conditions. As superficial velocity is lowered, the pressure drop, bed shrinkage and band velocity are all reduced. The band length is not affected.

The following are examples of the present invention. They are designed as illustrations only, and should not be interpreted to limit the scope of the invention.

Example 1

In order to prove the concept of the invention, an experimental system was designed to form and drive, in a column packed with mixed-charge resins, at least one feed band by its corresponding displacer in acidic, alkaline, or neutral states. The experimental system was also capable of alternating the acidic and alkaline states in processing the feed-displacer combinations, with or without de-ionized water washing of the remaining displacer after each combination run. The column itself consisted of a glass tube fitted with two adjustable-length bed supports. Retaining frits and distributors held the resins in place. Water jacket cooling was employed to remove the heat of reaction and maintain the column temperature, when needed.

The feed and displacer solutions were delivered to the column through a switching valve equipped with multiple loops. In this example, during loading, the $H_2SO_3$ feed loop and the $H_2SO_4$ displacer loop were filled while the water was flushing the mixed-charge resin column. When the valve switched to feeding, carrier water pushed the $H_2SO_4$ displacer, which in turn pushed the $H_2SO_3$ feed. In this manner, the feed band was formed and continuously driven by the displacer in the mixed-charge resin column. The conductivity meter with an in-line cell was incorporated to monitor the column effluent and to locate the feed band. Samples were taken from the $H_2SO_3$ feed band for sulfur isotope analysis on a mass spectrometer. A back-pressure regulator was needed to maintain a high enough pressure to keep $SO_2$ gas in solution.

After completing the $H_2SO_3$ feed and $H_2SO_4$ displacer run, the mixed-charge resin column was flushed with de-ionized water to remove excess $H_2SO_4$ remaining in the mixed-charge resin bed. Then, the $NH_4OH$ feed and $NaOH$ displacer solutions were, similarly, delivered to the mixed-charge resin column, using the switching valve and the $NH_4OH$ and $NaOH$ loops. The samples of the $NH_4OH$ feed band were also collected for nitrogen isotope analysis on a mass spectrometer.

The spectral analyses of sulfur and nitrogen isotopes on a mass spectrometer required the conversions of their feed band samples to dry gas samples. The $H_2SO_3$ feed samples were converted to $SO_2$ gas by adding concentrated $H_2SO_4$ solution, and the $NH_4OH$ feed samples to $N_2$ gas by first adding concentrated $HCl$ solution for conversion to $NH_4Cl$ and later adding concentrated $NaOBr$ solution to dried $NH_4Cl$ for final conversion. The results of this experiment are shown in Table 1.

TABLE 1

| TEST CONDITIONS AND RESULTS | |
|---|---|
| Column Height (cm) | 50 |
| Column ID (cm) | 0.5 |
| Resin Bed Height (cm) | 46 |
| Anion Resin Type and Initial Form | Benson BA-X12, OH-form |
| Cation Resin Type and Initial Form | Benson BC-X12, Na-form |
| Capacity Ratio - Anion:Cation | 1:2 |
| Flow Rate - ml/min | 0.156 |
| Temperature (°C.) | 23 |
| Pressure (psig) | 330–470 |
| Back-Pressure (psig) | 0–300 |
| Sulfur Feed | 2.5 ml 0.35$\underline{M}$ $H_2SO_3$ (Nat. Abund. = 4.22% $^{34}S$) |
| Sulfur Displacer | 0.35$\underline{M}$ $H_2SO_4$ |
| Operating Mode | $H_2SO_3$ band displaced by $H_2SO_4$ and |

TABLE 1-continued
TEST CONDITIONS AND RESULTS

| | |
|---|---|
| | $NH_4OH$ band displaced by NaOH |
| Nitrogen Feed | 5 ml 0.5$\underline{M}$ $NH_4OH$ (50% $^{15}N$) |
| Nitrogen Displacer | 0.6$\underline{M}$ NaOH |
| Average Sulfur Band Velocity (cm/min) | 0.54 |
| Sulfur Band Length (cm) | 4.7 |
| Average Nitrogen Band Velocity (cm/min) | 0.3 |
| Nitrogen Band Length (cm) | 7.1 |
| $^{34}S$ Product Range (%) | 4.0–4.5 |
| $^{15}N$ Product Range (%) | 22.5–73.5 |

Example 2

This experiment was run as described in Example 1, except that the test conditions and results were as follows. The major changes were made on Column ID and Capacity Ratio.

TABLE 2
TEST CONDITIONS AND RESULTS

| | |
|---|---|
| Column Height (cm) | 50 |
| Column ID (cm) | 0.63 |
| Resin Bed Height (cm) | 37 |
| Anion Resin Type and Initial Form | Benson BA-X12, OH-form |
| Cation Resin Type and Initial Form | Benson BC-X12, Na-form |
| Capacity Ratio - Anion:Cation | 1:1 |
| Flow Rate - ml/min | 0.312 |
| Temperature (°C.) | 23 |
| Pressure (psig) | 80–290 |
| Back-Pressure (psig) | 0–100 |
| Sulfur Feed | 1.5 ml 0.97$\underline{M}$ $H_2SO_3$ (Nat. Abund. = 4.22% $^{34}S$) |
| Sulfur Displacer | 0.5$\underline{M}$ $H_2SO_4$ |
| Nitrogen Feed | 3 ml 0.5$\underline{M}$ $NH_4OH$ (50% $^{15}N$) |
| Nitrogen Displacer | 0.5$\underline{M}$ NaOH |
| Operating Mode | $H_2SO_3$ band displaced by $H_2SO_4$ and $NH_4OH$ band displaced by NaOH |
| Average Sulfur Band Velocity (cm/min) | 0.51 |
| Sulfur Band Length (cm) | 2.6 |
| Average Nitrogen Band Velocity (cm/min) | 0.55 |
| Nitrogen Band Length (cm) | 4.4 |
| $^{34}S$ Product Range (%) | 3.9–4.6 |
| $^{15}N$ Product Range (%) | 40.7–61.9 |

EXAMPLE 3

This experiment was run according to the protocol of Example 1, except that the test conditions and results were as follows. The major changes were made on Operating Mode as well as on Column ID and Capacity Ratio. In this operating mode the $H_2SO_3$ feed and $H_2SO_4$ displacer solutions were directly driven by the $NH_4OH$ feed and NaOH displacer solutions, as a single run, without an interruption for de-ionized water washing of $H_2SO_4$.

TABLE 3
TEST CONDITIONS AND RESULTS

| | |
|---|---|
| Column Height (cm) | 50 |
| Column ID (cm) | 0.63 |
| Resin Bed Height (cm) | 37 |
| Anion Resin Type and Initial Form | Benson BA-X12, OH-form |
| Cation Resin Type and Initial Form | Benson BC-X12, Na-form |

TABLE 3-continued
TEST CONDITIONS AND RESULTS

| | |
|---|---|
| Capacity Ratio - Anion:Cation | 1:1 |
| Flow Rate - ml/min | 0.312 |
| Temperature (°C.) | 23 |
| Pressure (psig) | 80–290 |
| Back-Pressure (psig) | 0–100 |
| Sulfur Feed | 1.5 ml 0.97$\underline{M}$ $H_2SO_3$ (Nat. Abund. = 4.22% $^{34}S$) |
| Sulfur Displacer | 10 ml 0.5$\underline{M}$ $H_2SO_4$ |
| Nitrogen Feed | 3 ml 0.5$\underline{M}$ $NH_4OH$ (50% $^{15}N$) |
| Nitrogen Displacer | 0.5$\underline{M}$ NaOH |
| Operating Mode | $H_2SO_3$, $H_2SO_4$, and $NH_4OH$ bands successively displaced by NaOH |
| Average Sulfur Band Velocity (cm/min) | 0.54 |
| Sulfur Band Length (cm) | 2.9 |
| Average Nitrogen Band Velocity (cm/min) | 0.55 |
| Nitrogen Band Length (cm) | 4.7 |
| $^{34}S$ Product Range (%) | 3.9–4.9 |
| $^{15}N$ Product Range (%) | 35.5–63.4 |

EXAMPLE 4

This experiment was run according to the same protocol as Example 1, except the test conditions and results were as follows in the table below.

This table ascertains that a series of adjacent feed bands having the same state ionic components (in this example, $HCO_3^-$ and $HSO_3^-$) can be displaced by a single common displacer having the corresponding ionic component (in this example, $HSO_4^-$). Thus, multi-band, multi-ionic operating modes can be employed in self-regenerating column chromatography for multiple products. For example, instead of one acidic feed band and one alkaline feed band as processed in Example 3, two acidic feed-bands and two alkaline feed-bands can be processed by their respective displacers in a train mode for producing four different isotopic products.

TABLE 4
TEST CONDITIONS AND RESULTS

| | |
|---|---|
| Column Height (cm) | 25 |
| Column ID (cm) | 0.63 |
| Resin Bed Height (cm) | 22 |
| Anion Resin Type and Initial Form | Benson BA-X12, OH-form |
| Cation Resin Type | None |
| Capacity Ratio - Anion:Cation | 100% anion |
| Flow Rate - ml/min | 0.312 |
| Temperature (°C.) | 45 |
| Pressure (psig) | 330–560 |
| Back-Pressure (psig) | 240 |
| Carbon Feed | 5 ml 0.3$\underline{M}$ $H_2CO_3$ (Nat. Abund. = 1.11% $^{13}C$) |
| Sulfur Feed | 10 ml 0.5$\underline{M}$ $H_2SO_3$ (Nat. Abund. = 4.22% $^{34}S$) |
| Sulfur Displacer | 0.6$\underline{M}$ $H_2SO_4$ |
| Nitrogen Feed | None |
| Nitrogen Displacer | None |
| Operating Mode | $H_2CO_3$ and $H_2SO_3$ bands displaced by $H_2SO_4$ |
| Average Carbon Band Velocity (cm/min) | 0.27 |
| Carbon Band Length (cm) | 3.24 |
| Average Sulfur Band Velocity (cm/min) | 0.28 |
| Sulfur Band Length (cm) | 2.16 |
| $^{13}C$ Product Range (%) | 0.26–2.34 |
| $^{34}S$ Product Range (%) | 3.34–6.60 |

EXAMPLE 5

This experiment was run according to the protocol of Example 1, except that the test conditions and results were as follows in the table below.

The cationic and anionic components ($NH_4^+$ and $HSO_3^-$) of the composite feed were simultaneously displaced in the single feed band by the corresponding ionic components ($Na^+$ and $HSO_4^-$) of the composite displacer.

TABLE 5
TEST CONDITIONS AND RESULTS

| | |
|---|---|
| Column Height (cm) | 50 |
| Column ID (cm) | 0.63 |
| Resin Bed Height (cm) | 37 |
| Anion Resin Type and Initial Form | Benson BA-X12, $HPO_4$-form |
| Cation Resin Type and Initial Form | Benson BC-X12, H-form |
| Capacity Ratio - Anion:Cation | 1:1 |
| Flow Rate - ml/min | 0.312 |
| Temperature (°C.) | 23 |
| Pressure (psig) | 90 |
| Back-Pressure (psig) | 0 |
| Sulfur and Nitrogen Feed | 3 ml 0.5$\underline{M}$ $NH_4SO_3$ (containing 4.22% $^{34}S$ and 50% $^{15}N$) |
| Sulfur and Nitrogen Displacer | 0.35$\underline{M}$ $NaHSO_4$ |
| Operating Mode | $NH_4SO_3$ composite feed band displaced by $NaHSO_4$ composite displacer |
| Average Band Velocity (cm/min) | 0.35 |
| Band Length (cm) | 6.64 |
| $^{34}S$ Product Range (%) | 3.9–4.92 |
| $^{15}N$ Product Range (%) | Insignificant and inconclusive |

While the invention has been described in connection with its preferred embodiments, it should be understood that changes and modifications may be made without departing from the scope of the appended claims.

What is claimed is:

1. A process for treating ions comprising,
   (a) delivering at least one ionic feed solution containing oppositely-charged ions in either acidic or alkaline state, to a mixed-charge bed;
   (b) delivering at least one ionic displacer solution containing oppositely-charged ions, in the same acidic or alkaline state as the ionic feed solution to the mixed-charge bed, and sequentially to the ionic feed solution; and
   (c) recovering desired ion or ions.

2. A process for treating ions comprising,
   (a) delivering at least one first ionic feed solution in either acidic or alkaline state, to a mixed-charge bed;
   (b) delivering a first ionic displacer solution in the same acidic or alkaline state as the first ionic feed solution, to the mixed-charge bed, and sequentially to the first ionic feed solution; and
   (c) delivering at least one second ionic feed solution having the acidic or alkaline state opposite to the first ionic feed and displacer solutions to the mixed-charge bed, and sequentially to the first ionic displacer solution; and
   (d) delivering a second ionic displacer solution having the same acidic or alkaline state as the second ionic feed solution, to the mixed-charge bed, and sequentially to the second ionic feed solution; and
   (e) repeating steps (a) through (d) as many times as desired, so long as the pairs of steps are alternating and the terminal step is either (b) or (d); and
   (f) recovering desired ions.

3. A process of claim 2, wherein the first and second ionic feed solutions comprise multiple solutions in the same acidic or alkaline state which move together, but in separate bands.

4. A process of claim 2, wherein steps (a) through (d) occur one time only.

5. A process of claim 1, wherein the ionic feed solution comprise specific isotopes in cationic, anionic or mixed (salt) form, and the isotopes are separated and enriched within the ionic feed band during the processing, for recovery.

6. A process of claim 2, wherein the ionic feed solutions comprise specific isotopes in cationic, anionic or mixed (salt) form, and the isotopes are separated and enriched within the ionic feed band during the processing, for recovery.

7. A process of claim 3, wherein the ionic feed solutions comprise specific isotopes in cationic, anionic or mixed (salt) form, and the isotopes are separated and enriched within each ionic feed band during the processing, for recovery.

8. A process of claim 6, wherein isotopes are separated, enriched and recovered from each ionic feed solution in an alternating cycle of alkaline displacer solutions and acidic displacer solutions, not necessarily in that order, but ensuring that an ionic feed solution in alkaline or neutral state is displaced by an alkaline displacer solution and an ionic feed solution in acidic or neutral state by an acidic displacer solution.

9. A process of claim 1, wherein the isotopes of two different elements are present in mixed (salt) form and are separated, enriched and recovered from the mixed feed solution simultaneously.

10. A process of claim 6, wherein the first and second ionic solutions comprise nitrogen isotopes in alkaline form and sulfur isotopes in acidic form, respectively.

11. A process of claim 5, wherein the ionic feed solutions comprise isotopes chosen from the group of elements consisting of: calcium, strontium, magnesium, chlorine and bromine.

12. A process of claim 2, wherein the mixed-charge bed comprises two resins with opposite charges.

13. A process of claim 2, wherein the mixed-charge bed comprises one resin with two opposite charges.

14. A process of claim 12, wherein the two resins have equal capacities.

15. A process of claim 12, wherein the two resins have unequal capacities.

16. A process of claim 12, wherein the resins are the sulfonated polystyrene-divinyl benzene copolymer resin and aminated polystyrene-divinyl benzene copolymer resin.

17. A process of claim 16, wherein the polystyrene-divinyl benzene copolymer resins are 12% crosslinked.

18. A process for treating ions wherein two separate resin phases of two opposite charges in a mixed-charge bed are separately and alternately regenerated when the displacer solutions of the opposite charge are being processed through a column of mixed-charge bed.

* * * * *